US007211410B2

(12) United States Patent
De Simone

(10) Patent No.: US 7,211,410 B2
(45) Date of Patent: May 1, 2007

(54) ANALYTICAL METHOD FOR DETECTING ALKALINE SPHINGOMYELINASE AND KIT FOR USE IN SUCH METHOD

(75) Inventor: Claudio De Simone, Ardea RM (IT)

(73) Assignee: VSL Pharmaceuticals, Inc., Gaithersburg, MD (US)

( * ) Notice: Subject to any disclaimer, the term of this patent is extended or adjusted under 35 U.S.C. 154(b) by 0 days.

(21) Appl. No.: 11/359,619

(22) Filed: Feb. 23, 2006

(65) Prior Publication Data

US 2006/0141551 A1    Jun. 29, 2006

Related U.S. Application Data

(60) Division of application No. 10/499,336, filed on Jun. 17, 2004, which is a continuation of application No. PCT/IT02/00811, filed on Dec. 19, 2002, now abandoned.

(30) Foreign Application Priority Data

Dec. 21, 2001  (IE)  ................................. 2001/1100

(51) Int. Cl.
*C12Q 1/44* (2006.01)
(52) U.S. Cl. ....................................................... 435/19
(58) Field of Classification Search .................... None
See application file for complete search history.

(56) References Cited

U.S. PATENT DOCUMENTS 6,265,179 B1    7/2001    Zhou et al.

FOREIGN PATENT DOCUMENTS

WO    WO 03/056031 A2    7/2003

OTHER PUBLICATIONS

Hertervig et al, "Alkaline Sphingomyelinase Activity is Decreased in Human Colorectal Carcinoma," (Cancer), 1997, vol. 79, pp. 448-453.*
Duan et al, "Effects of Ursodeoxycholate and Other Bile Salts on Levels Of Rat Intestinal Alkaline Sphingomyelinase: A Potential Implication in Tumorigenesis," (Dig Dis & Sci), Jan. 1998, vol. 43, No. 1, pp. 26-32.*
Molecular Probes Inc., Invitrogen Corporation, "Product Information: Amplex Red Sphingomyelinase Assay Kit (A12220)".*
Denisova Natalia A et al: "Role of membrane lipids in regulation of vulnerability to oxidative stress in PC12 cells: Implication for aging." Free Radical Biology & Medicine, vol. 30, No. 6, Mar. 15, 2001, pp. 671-678, XP002255204 ISSN: 0891-5849 p. 673.
Sofic E et al: "Antioxidant and pro-oxidant capacity of catecholamines and related compounds. Effects of hydrogen peroxide on glutathione and spingomyelinase activity in pheochromocytoma PC12 cells: Potential relevance to age-related diseases." Journal of Neural Transmission, vol. 108, No. 5, 2001, pp. 541-557, XP002255205 ISSN: 0300-9564 p. 544-p. 545.

(Continued)

*Primary Examiner*—Christopher R. Tate
*Assistant Examiner*—Amanda P. Wood
(74) *Attorney, Agent, or Firm*—Nixon & Vanderhye P.C.

(57) ABSTRACT

An analytical fluorometric method and a kit for use in such method are disclosed for assessing the presence of alkaline sphingomyelinase (SMase) in the stool of a patient in need of such an assessment since alkaline SMase is a marker of serious pathological states, such as colon cancer.

1 Claim, 1 Drawing Sheet

Detection of sphingomyelinase using the fluorescence assay.
Each reaction contained the indicated amount of bacteric sphingomyelinase in specific assay buffer.
Reactions were incubated at 37°C for one hour. Fluorescence was measured with a fluorescence microplate reader using excitation at 530 nm and fluorescence detection at 590 nm.

OTHER PUBLICATIONS

Goni F M et al: "Sphingomyelinases: enzymology and membrane activity" FEBS Letter, Elsevier Science Publishers, Amsterdam, NL, vol. 531, No. 1, Oct. 30, 2002, pp. 38-46, XP004389130 ISSN: 0014-5793 p. 42.

He Xingxuan et al: "A Fluorescence-Based, High-Throughput Sphingomyelin Assay for the Analysis of Niemann-Pick Disease and Other Disorders of Sphingomyelin Metabolism." Analytical Biochemistry, vol. 306, No. 1, Jul. 1, 2002, pp. 115-123, XP002255206 Jul. 1, 2002, ISSN: 003-26797 Abstract.

Amplex® Red Sphingomyelinase Assay Kit (A12220), Molecular Probes, Product Information, Revised: Oct. 1, 2004.

Invitrogen Corporation Molecular Probes, "Product Information: Amplex Red Sphingomyelinase Assay Kit (A1220)", 4 pages.

Biocompare Website Printout, "Amplex Red Sphingomyelinase Assay Kit", first available on web 1999, 3 pages.

Email Communication Printout, Amplex Red Sphingomyelinase Assay Kit (A1222), Product Availability May 12, 1999, dated Oct. 20, 2005.

Molecular Probes Invitrogen Detection Technologies, "Amplex Red Sphingomyelinase Assay Kit (A12220)" Product Information, Revised Oct. 2004, p. 1-4.

* cited by examiner

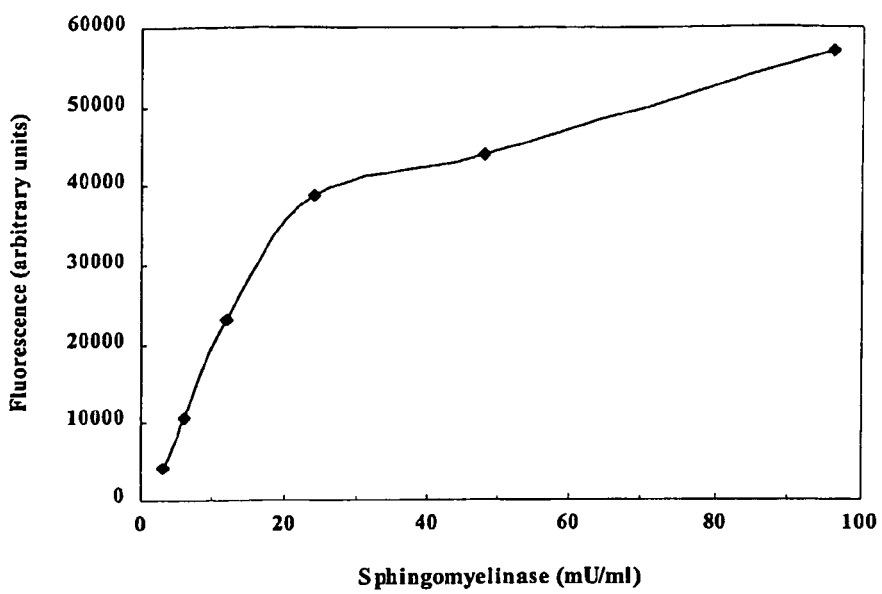
*Figure 1.* Detection of sphingomyelinase using the fluorescence assay.
Each reaction contained the indicated amount of bacteric sphingomyelinase in specific assay buffer.
Reactions were incubated at 37°C for one hour. Fluorescence was measured with a fluorescence microplate reader using excitation at 530 nm and fluorescence detection at 590 nm.

ANALYTICAL METHOD FOR DETECTING ALKALINE SPHINGOMYELINASE AND KIT FOR USE IN SUCH METHOD

This application is a divisional of application Ser. No. 10/499,336 filed Jun. 17, 2004 now abandoned, which in turn is a U.S. national phase of international application PCT/IT02/00811 filed 19 Dec. 2002, which designated the US. PCT/IT02/00811 claims priority to IE Application No. 011100 filed 21 Dec. 2001. The entire contents of these application are incorporated herein by reference.

The present invention relates to an analytical method for assessing the presence of alkaline sphingomyelinase in the stools or biological fluids of patients in need of such an assessment. The invention also relates to a kit for carrying out the analytical method.

More particularly the method of the present invention is an in vitro fluorometric method for detecting alkaline sphingomyelinase which, as will be described in detail hereinbelow, is a marker of serious pathological states such as colon cancer and familial adenomatous polyposis.

The enzyme sphingomyelinase (sphingomyelin phosphodiesterase, SMase) catalyzes the hydrolysis of sphingomyelin to ceramide and choline phosphate.

Three different types of SMase (acidic, neutral and alkaline) have been identified to-date, which occur as several iso-forms, as follows:

lysosomal acidic SMase (A-SMase);
cytosolic $Zn^{2+}$-dependent acidic SMase;
membrane neutral magnesium-dependent SMase (N-SMase);
cytosolic magnesium-independent N-SMase; and
alkaline SMase.

SMases have been shown to play a role in a wide variety of physiologic and pathological processes, including: lysosomal hydrolysis of endocytosed SM, ceramide mediated cell signalling, atherogenesis, terminal differentiation, cell cycles arrest, apoptosis, inflammation, and the regulation of eukaryotic stress responses.

In contrast to acidic and neutral SMase, which are currently present in cells as lysosomal and membrane-bound enzymes, respectively, alkaline SMase exhibits tissue and species difference. In human beings, the alkaline SMase is found in intestinal mucosa and bile. Alkaline SMase starts to appear in the duodenum, reaches a high level in the intestine, especially in the distal part of the jejunum, and occurs in considerable amounts in the colon and rectum. This SMase presents optimal alkaline pH at 9.0, is $Mg^{2+}$-independent, bile salt-dependent and trypsin-resistant.

The pathological importance of alkaline SMase has only recently been recognized and this has prompted several studies to be carried out, mainly for the following reasons.

First, the enzyme may be responsible for the hydrolysis of the dietary sphingomyelin occurring substantially in milk, eggs, meat and fish. Second, this enzyme may regulate cholesterol absorption. Third, the presence of alkaline SMase along the intestinal tract and its selective decrease detected in colorectal carcinoma suggests that this enzyme plays a role in intestinal carcinogenesis, since under physiological conditions, it stimulates apoptosis and protects the intestinal mucosa against carcinogenesis.

Previous studies have also shown that, under physiological conditions, alkaline SMase is dissociated by bile salts from intestinal mucosal membrane to the lumen. However, under pathological conditions, whereby bile salt concentration is abnormally increased, the dissociation of alkaline SMase by bile salts may exceed the biosynthesis of the enzyme, resulting in a low level of activity of alkaline SMase in the mucosa, and an abnormally increased excretion of the enzyme in the faeces or in biological fluids, i.e. bile. Consequently, the excess of alkaline SMase excreted in the stools or in biological fluids over normal, basal values, may be interpreted as a valuable diagnostic marker for colon rectal carcinoma and familial adenomatous polyposis, hence; the need of a reliable assay for detecting alkaline SMase in the stools or in biological fluids of patients likely to be suffering from the aforesaid pathologies of the intestinal tract.

In addition, some bacteria strains (e.g. *Streptococcus termophilus Lactobacilli*) contain high levels of SMase, and the assessment of alkaline SMase may provide a method to evaluate changes in the number of said bacteria, i.e. after a treatment with probiotics or/and probiotic-based products.

Previous methods for assaying alkaline SMase are already known. The activity of the SMases can be determined either in vivo through cell labelled with a radioactive precursor of SM and then determining the labelling product levels or in vitro using radiolabelled SM or a chromogenic analog of SM or colored and fluorescent derivatives of neutral SM.

These known commonly used assays are not entirely satisfactory since they are potentially very hazardous insofar as they are radioactive assays and less sensitive than a fluorometric assay.

An object of the present invention is to provide a reliable, unexpensive assay for alkaline SMase in the stools or biological fluids of patients likely to suffer from colorectal carcinoma and familial adenomatous polyposis, or gall bladder or liver diseases, which overcomes the drawbacks of the known methods.

A further object of the present invention is to provide an analytical kit for use in the aforesaid assay.

Another object of the present invention is the assessment of bacterial colonization in different health conditions or following diseases or treatment with drugs or probiotics or food supplements.

The fluorometric, indirect assay method of the present invention is grounded on the following sequence of reactions.

Under the action of alkaline SMase, present in faeces or other biological fluids, sphingomyelin is hydrolyzed to ceramide and phosphorylcholine which, under the action of alkaline phosphatase, is hydrolyzed yelding choline. In the presence of choline oxidase, choline produces hydrogen peroxide ($H_2O_2$).

This latter compound, in the presence of horse-radish peroxidase, is caused to react with 10-acetyl-3.7-dihidroxyphenoxazine, a sensitive fluorogenic probe for $H_2O_2$ (hereinbelow referred to as "Amplex Red Reagent") yelding the highly fluorescent compound resorufin. Fluorescence is measured with a fluorocount microplate fluorometer using excitation at 530–560 nm and fluorescence detection at 590 nm.

Based on the aforesaid reaction sequence and fluorescence detection means, the assay method of the present invention for assaying alcaline SMase comprises the following steps which refers to stools. However, it will be apparent to a person skilled in the art that this method can be easily applied also to biological fluids such as bile with appropriate routine variations, 1) collecting a sample of a patient's stools and drying it up;
2) weighing about 3–4 grams of the dried up sample and suspending it in 20 ml of a homogenization buffer containing 0.25 M sucrose, 0.15 M KCl, 50 mM $KH_2PO_4$, pH 7.4;

3) centrifuging the sample at 4000 rpm at +4° C. for 60 min;
4) recovering the supernatant and centrifuging again for 15 min. at 4000 rpm at +4° C.;
5) measuring protein content in supernatant with the Pierce Protein Assay with bovine serum albumine as standard using for each sample a range of protein concentration between 32 mg/ml and 40 mg/ml and pipetting 25 µl of each sample into well;
6) adding to each 25 µl sample 65 µl of assay buffer containing 50 mM Tris/HCl, 2 mM EDTA, 0.15 M NaCl pH 9.0 and 10 µl of 29 µM sphingomyelin and in assay buffer adding bile salts (TC, TDC, GC, GCDC) in the concentration of 3 mM;
7) incubating at 37° C. for 1 hr;
8) pipetting 100 µl of each standard (see below) and 10 µl of sphingomyelin (29 µM), incubating for 1 hr at 37° C. as the samples;
9) after 1 hour, adding 100 µl of reaction buffer containing 50 mM Tris/HCl pH 7.4, 10 mM β-glycerophosphate, 750 µM ATP, 5 mM EDTA, 5 mM EGTA, 100 µM Amplex Red, 8 U/ml alkaline phosphatase, 0.2 U/ml choline oxidase, 2 U/ml horseradish peroxidase;
10) incubating the reactions for 1 hour or longer at 37° C., protected from light;
11) measuring the fluorescence in a fluorescence microplate reader using excitation in the range of 530–560 nm and emission detection at 590 nm;
12) for each point, correcting for background fluorescence by subtracting the values derived from the no-sphingomyelinase control.

The invention also relates to a kit for detecting alkaline sphingomyelinase in a patient's stools or biological fluids according to the previously disclosed method, which comprises test tubes separately containing samples of the following reagents:
a) sphingomyelin to be hydrolized by alkaline sphingomyelinase present in the stools or biological fluids, to give phosphorylcholine;
b) alkaline phosphatase for catalyzing the hydrolysis of phosphorylcholine to choline;
c) choline oxidase for oxidizing choline to hydrogen peroxide;
d) horse-radish peroxidase for assisting reaction of hydrogen peroxide with
e) Ampler Red Reagent (10-acetyl-3.7-dihydroxyphenoxazine) to give the fluorescent compound resorufin whose fluorescence is a marker of the alkaline SMase present in the stools or biological fluids; and
f) lyophilized bacterial sphingomyelinase for use as standard concentrate.

For the analytical method of the present invention to be suitably carried out, in addition to the aforesaid kit components, the following further materials and equipments are required:
Sucrose;
Potassium chloride (KCl);
Potassium phosphate, monobasic ($KH_2PO_4$);
Trizma base;
EDTA;
Sodium chloride;
Taurocholate (TC);
Taurodeoxycholate (TDC);
Glycocholate (GC);
Glycochenodeoxycholate (GCDC);
β-glycerophosphate;
ATP disodium salt;
EGTA;
BCA Protein Assay Reagent;
Bovine serum albumine;
A refrigerated centrifuge;
A microplate reader capable of measurement at 550–562 nm, and
A fluorocount microplate fluorometer.

In order to accomplish the quantification of SMase activity, the following measures should be taken.

STANDARD CURVE PREPARATION

The kit is supplied with a standard preparation of SMase, it consists of bacterial extract containing a type of SMase that works at pH 9. The following operations should be performed.

Generate a SMase calibration curve: dilute the standard concentrate to make serial dilutions.

Reconstitute the SMase standard with 1 ml of assay buffer (pH 9.0); this reconstitution produces a stock solution of 96 mU/ml.

Pipette 0.500 ml of assay buffer into each tube. Use the stock solution to produce a dilution series. Mix each tube thoroughly before the next transfer. The undiluted standard serves as the high standard (96 mU/ml), and the standard curve will contain the following concentrations (mU/ml): 96-48-24-12-6-3. Buffer serves as the zero standard (0 mU/ml).

TYPICAL STANDARD CURVES

In FIG. 1 the standard curve is shown for demonstration only. A standard curve should be generated for each set of samples assayed.

CALCULATION OF RESULTS

Average the duplicate readings for each standard and sample and subtract the average zero standard fluorescence.

Plot the fluorescence for the standards versus the activity (mU/ml) of the standards and draw the best curve. To determine the SMase activity of each sample, first find the fluorescence value on the y-axis and extend a horizontal line to the standard curve. At the point of intersection, extend a vertical line to the x-axis and read the corresponding SMase activity.

The described method is able to assay SMase activity in vitro; it has been developed with the intent to detect alkaline SMase in an organic sample.

To assay specifically the alkaline SMase the method uses conditions that detect the acid and neutral SMases activity. In fact:
the homogenization buffer is at neutral pH, but it have not protease and phosphatase inhibitors to exclude the neutral SMase since the latter is sensitive to activities of proteases and phosphatases and is consequently inhibited by these enzymes;
in the homogenization buffer the $MgCl_2$ is absent to block the activity of Mg dependent neutral SMase;
the reaction buffer contains β-glycerophosphate and ATP to preclude acid SMase moreover activity at neutral pH, in this buffer EDTA and EGTA are present in high concentration to inhibit neutral SMase.

What is claimed is:
1. A method for detecting alkaline sphingomyelinase in a patient'stool, which comprises:
(a) collecting a sample of a paient's stool and drying the sample;

(b) weighting about 3–4 grams of the dried sample and suspending it in 20 mL of a homogenization buffer containing 0.25 M sucrose, 0.15 M KCl, and 50 mM $KH_2PO_4$ pH 7.4;

(c) centrifuguing the suspended sample at 4000 rpm at +4° C. for 60 min to obtain a supernatant;

(d) recovering the supernatant and centrifuging again for 15 min at 4000 rpm at +4° C.;

(e) measuring protein content in the supernatant with a Pierce Protein Assay and pipetting 25 µl of the supernatant sample with a protein concentration between 32 mg/mL and 40 mg/mL into wells of a microplate;

(f) adding to each 25 µl supernatant sample 65 µl of assay buffer containing 50 mM Tris/HCl, 2 mM EDTA, 0.15 M NaCl pH 9.0, 10 µl of 29 µM sphingomyelin, and bile salts selected from TC, TDC, GC and GCDC at a concentration of 3 mM;

(g) incubating at 37° C. for 1 hr;

(h) pipetting into wells of a microplate 10 µl of sphingomyelin (29 µM) and 100 µl of known concentrations of bacterial sphingomyelinase in assay buffer generated from a standard curve prepared from a standard sphingomyelinase concentrate active at pH 9.0, and incubating at 37° C. for 1 hr;

(i) after 1 hour, adding to each well 100 µl of reaction buffer containing 50 mM Tris/HCl pH 7.4, 10 mM β-glycerophosphate, 750 µM ATP, 5 mM EDTA, 5 mM EGTA, 100 µM Amplex Red, 8 U/mL alkaline phosphatase, 0.2 U/mL choline oxidase, and 2 U/mL horseradish peroxidase;

(j) incubating the reactions for 1 hour or longer at 37° C., protected from light;

(k) measuring fluorescence of samples and known concentrations of standard in a fluorescence microplate reader using excitation in the range of 530–560 nm and emission detection at 590 nm to obtain fluorescence values; and (l) correcting for background fluorescence by subtracting the value derived from the zero standard sphingomyelinase control.

* * * * *